(12) United States Patent  
Larson et al.

(10) Patent No.: US 8,273,044 B1
(45) Date of Patent: Sep. 25, 2012

(54) TRACTION SPLINT DEVICE

(76) Inventors: Donald O. Larson, Audubon, MN (US); Kasey P. Larson, Detroit Lakes, MN (US)

( * ) Notice: Subject to any disclaimer, the term of this patent is extended or adjusted under 35 U.S.C. 154(b) by 405 days.

(21) Appl. No.: 12/631,527

(22) Filed: Dec. 4, 2009

(51) Int. Cl.
*A61F 5/00* (2006.01)
(52) U.S. Cl. .............................. 602/23; 602/32; 128/882
(58) Field of Classification Search ................ 602/5, 23, 602/32, 26–27, 36, 62; 128/869, 882
See application file for complete search history.

(56) References Cited

U.S. PATENT DOCUMENTS

| | | | |
|---|---|---|---|
| 2,198,908 A | 4/1940 | Ellis | |
| 2,817,333 A | 12/1957 | Cole | |
| 3,477,428 A | 11/1969 | Hare | |
| 3,756,227 A | 9/1973 | Sager | |
| 3,762,405 A | 10/1973 | DeGeorge | |
| 3,804,085 A | 4/1974 | Eshuis et al. | |
| 3,906,942 A | 9/1975 | Lumb, Jr. et al. | |
| 3,909,942 A * | 10/1975 | Ciaffone | 30/47 |
| 4,265,230 A * | 5/1981 | Jordon | 602/23 |
| 4,328,794 A | 5/1982 | Holmes | |
| 4,336,796 A | 6/1982 | Andrews et al. | |
| 4,708,131 A | 11/1987 | Kendrick | |
| 4,911,152 A | 3/1990 | Barnes et al. | |
| 5,101,815 A | 4/1992 | Landon-Orr et al. | |
| 7,052,479 B2 | 5/2006 | Drennan | |
| 2006/0184083 A1 | 8/2006 | Buckman et al. | |

* cited by examiner

*Primary Examiner* — Patricia Bianco
*Assistant Examiner* — Camtu Nguyen
(74) *Attorney, Agent, or Firm* — Neustel Law Offices (57) ABSTRACT

A traction splint device for providing aid to a person suffering from a broken or fractured lower extremity. The device generally includes a collapsible shaft adapted to be positioned alongside a leg of a patient, a first support connected to a first end of the shaft, and a second support connected to a second end of the shaft. The first support is adapted to be positioned forwardly of a lower end of the leg and includes a center brace having a notch. A plurality of stabilizing straps traverse the shaft and are adapted to constrain the leg. At least one of the straps is adapted to wrap around the notch of the center brace to secure a lower end of the leg and at least one of the straps is adapted to extend through an opening of the second support to secure an upper end of the leg.

20 Claims, 8 Drawing Sheets

TRACTION SPLINT DEVICE

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to a splint and more specifically it relates to a traction splint device for efficiently providing aid to a person suffering from a broken or damaged lower extremity, such as but not limited to the femur.

2. Description of the Related Art

Any discussion of the related art throughout the specification should in no way be considered as an admission that such related art is widely known or forms part of common general knowledge in the field.

Splint devices have been in use for years to stabilize a person's leg when they are suffering from a broken, fractured, or damaged lower extremity, such as a femur, thigh bone, etc. Prior art splints generally fail in that they do not sufficiently stay affixed to the individual during movement. In addition, prior art splints can be uncomfortably to wear and difficult to affix to the lower extremity of the person. Because of the inherent problems with the related art, there is a need for a new and improved traction splint device for efficiently providing aid to a person suffering from a broken or damaged lower extremity, such as but not limited to the femur.

BRIEF SUMMARY OF THE INVENTION

A system for efficiently providing aid to a person suffering from a broken or damaged lower extremity, such as but not limited to the femur. The invention generally relates to a splint which includes a collapsible shaft adapted to be positioned alongside a leg of a patient, a first support connected to a first end of the shaft, and a second support connected to a second end of the shaft. The first support is adapted to be positioned forwardly of a lower end of the leg and includes a center brace having a notch. A plurality of stabilizing straps traverse the shaft and are adapted to constrain the leg. At least one of the straps is adapted to wrap around the notch of the center brace to secure a lower end of the leg and at least one of the straps is adapted to extend through an opening of the second support to secure an upper end of the leg.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview

Turning now descriptively to the drawings, in which similar reference characters denote similar elements throughout the several views, FIGS. 1 through 8 illustrate a traction splint device 10, which comprises a collapsible shaft 20 adapted to be positioned alongside a leg 12 of a patient, a first support 30 connected to a first end 21 of the shaft 20, and a second support 40 connected to a second end 22 of the shaft 20. The first support 30 is adapted to be positioned forwardly of a lower end of the leg 12 and includes a center brace 34 having a notch 36. A plurality of stabilizing straps 50-54 traverse the shaft 20 and are adapted to constrain the leg 12. At least one of the straps 50 is adapted to wrap around the notch 36 of the center brace 34 to secure a lower end of the leg 12 and at least one of the straps 51 is adapted to extend through an opening 44 of the second support 40 to secure an upper end of the leg 12.

B. Shaft

The shaft 20 is comprised of an elongated and tubular structure sufficient to extend the full length of a leg 12 of a patient. The shaft 20 is also comprised of a rigid structure, such as but not limited to aluminum alloy, to securely hold the leg 12 in place when secured to the shaft 20. The shaft 20 is also generally substantially lightweight and relatively small in diameter to not be cumbersome to the individual when utilizing the device 10.

The shaft 20 is also generally comprised of a collapsible structure, thus having a first segment 24 and a second segment 25 that are removably detachable from one another. The first segment 24 and the second segment 25 are generally comprised of similar lengths and structures. It is appreciated that the first segment 24 is generally located adjacent to and connected to the first support 30 and the second segment 25 is generally located adjacent to and connected to the second support 40. The first segment 24 and the second segment 25 also generally attach in a telescopic manner, thus one of the segments 25 having an extension 26 that is able to be linearly inserted within the other 24.

The first segment 24 and the second segment 25 are permanently connected internally via an internal connector 28. The internal connector 28 is preferably comprised of a resilient cord, such as but not limited to a bungee cord structure. The internal connector 28 is thus able to expand and retract to allow the first segment 24 to be pulled away and disconnected from the second segment 25 during transport or storage of the device 10 and to allow the first segment 24 and the second segment 25 to attach to each other via pulling the first segment 24 and the second segment 25 towards each other when aligned with each other.

C. First Support

The first support 30 is preferably connected to the first segment 24 of the shaft 20 at the first end 21, preferably via the first end 21 extending through the body 31 of the first support 30. The first support 30 may be comprised of various rigid and lightweight materials capable of supporting a strap 50 in a fixed position relative the lower end of the leg 12.

In the preferred embodiment, the first support 30 includes a pair of outer walls 32 extending upwardly from the body 31 of the first support 30. The outer walls 32 are spaced apart and flush with opposing sides of the body 31. Positioned between the outer walls 32 is a center brace 34 that also extends upwards from the body 31. The center brace 34 is spaced from each of the outer walls 32 and centrally located upon the body 31 to allow room for the strap 50 to wrap around the notch 36 located at the front of the center brace 34 and extend along each side of the center brace 34.

The notch 36 preferably extends downwardly and rearwardly from the top surface 35 of the center brace 34 to force the strap 50 downward against the body 31 thus preventing the strap 50 from sliding off of the center brace 34. The center brace 34 also preferably includes a projection 39 extending forwardly from the notch 36 at the top surface 35 to provide a stopping point for the strap 50 if the strap 50 were to slide upwardly on the notch 36.

The top surface 35 of the center brace 34 also preferably extends upwardly beyond the outer walls 32 and the notch 36 is positioned above the outer walls 32 to allow for the strap 50 to be more easily positioned around the center brace 34 within the notch 36. The notch 36 may extend to the body 31 or to a lower support 37 of the notch 36 that assists in stabilizing the center brace 34 upon the body 31 by adding strength to the first support 30.

D. Second Support

The second support 40 is preferably connected to the second segment 25 of the shaft 20 at the second end 22, preferably via the second end 22 extending through the body 41 of the second support 40. The second support 40 may be comprised of various rigid and lightweight materials capable of supporting a strap 51 in a fixed position relative the upper end of the leg 12.

In the preferred embodiment, the second support 40 includes a loop portion 43 extending from an outer end of the body 41 to form an opening 44 extending through thereof. The opening 44 is used to receive the strap 51 to affix the strap 51 to the device 10. The opening 44 may be comprised of various shapes, such as circular, semi-circular, etc.

E. Straps

The straps are used to secure the device 10 to the leg 12 of the patient. The present invention preferably includes a plurality of straps 50-54 to be located at spaced apart intervals along the shaft 20 and also extend from the first support 30 and the second support 40. The straps 50-54 are generally adjustable to accommodate for different width legs 12 and are comprised of a generally non-stretchable material that is comfortable when placed around ones skin, such as nylon. The straps 50-54 may adjusted in various manners, such as through the use of a hook and loop structure.

Figure 1:
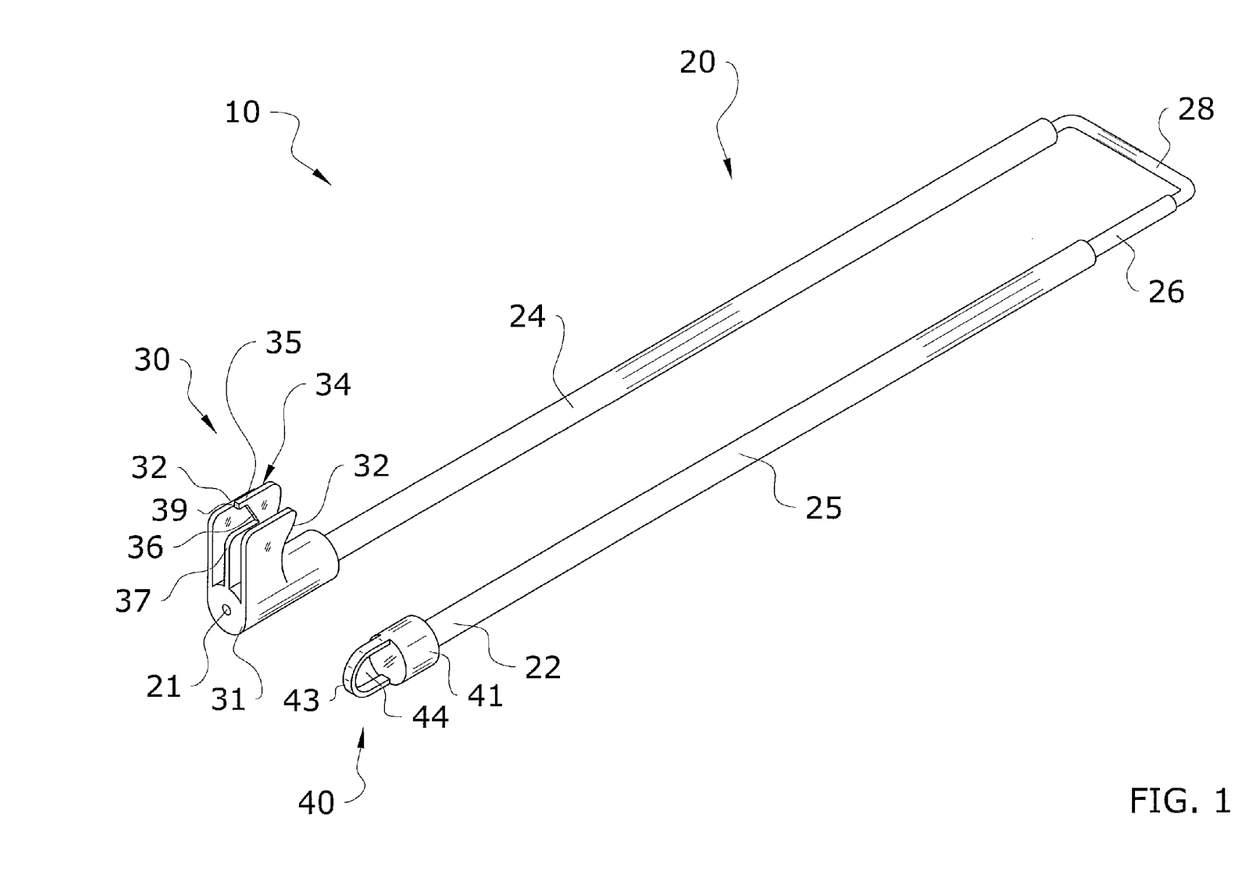
FIG. 1 is an upper perspective view of the device in a collapsed position.
Figure 2:
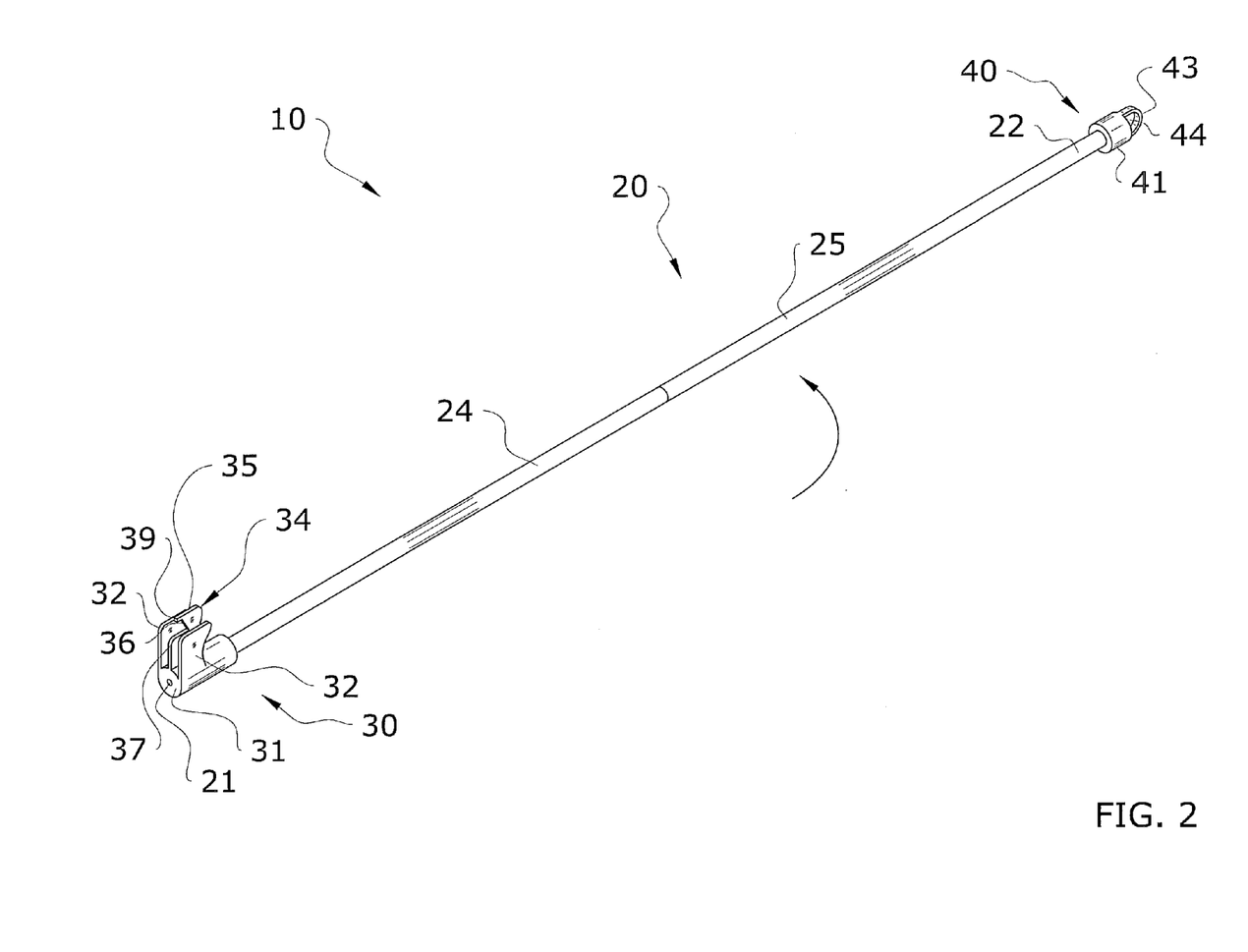
FIG. 2 is an upper perspective view of the device in an extended position.
Figure 3:
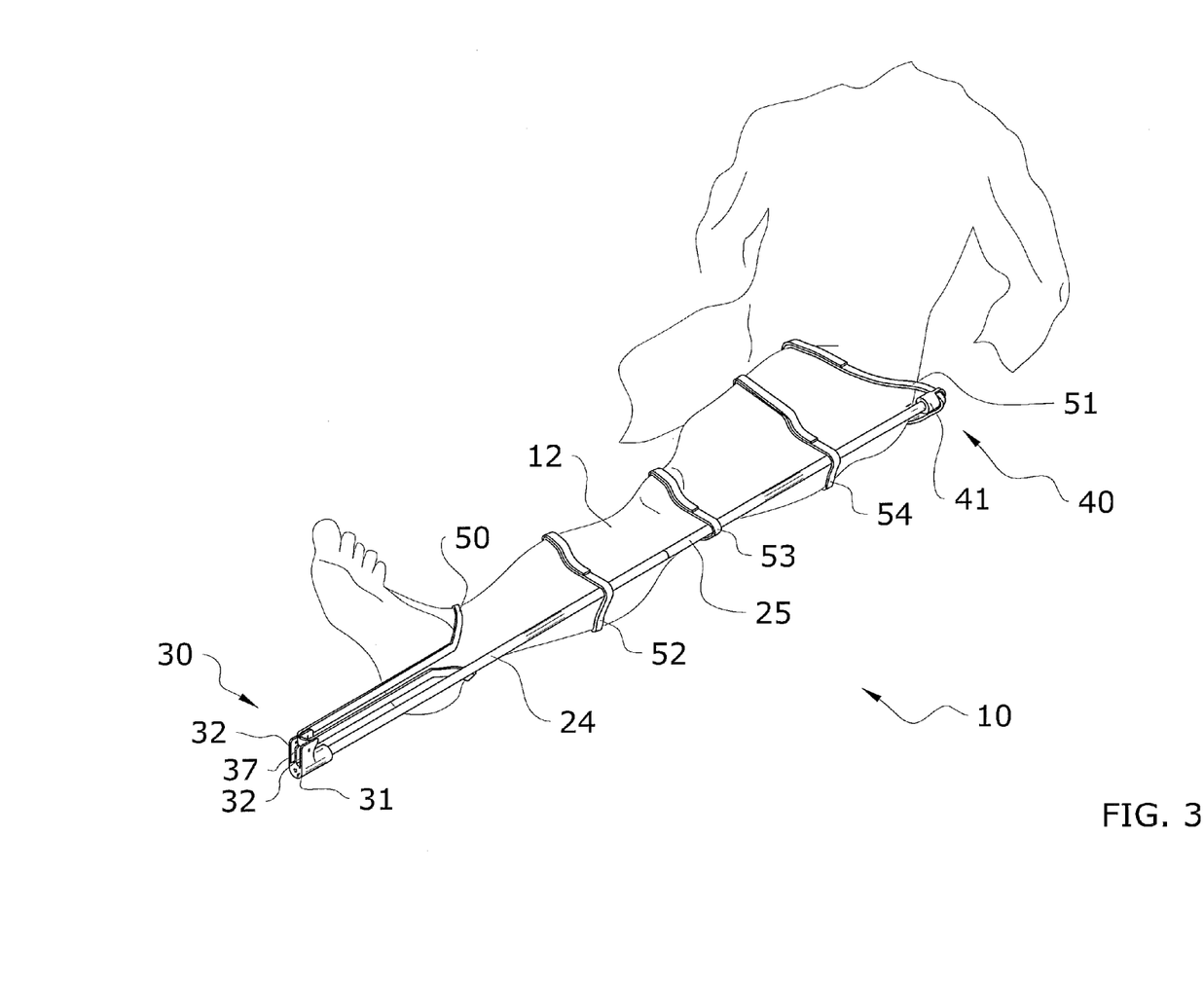
FIG. 3 is an upper perspective view of the present invention in use.
Figure 4:
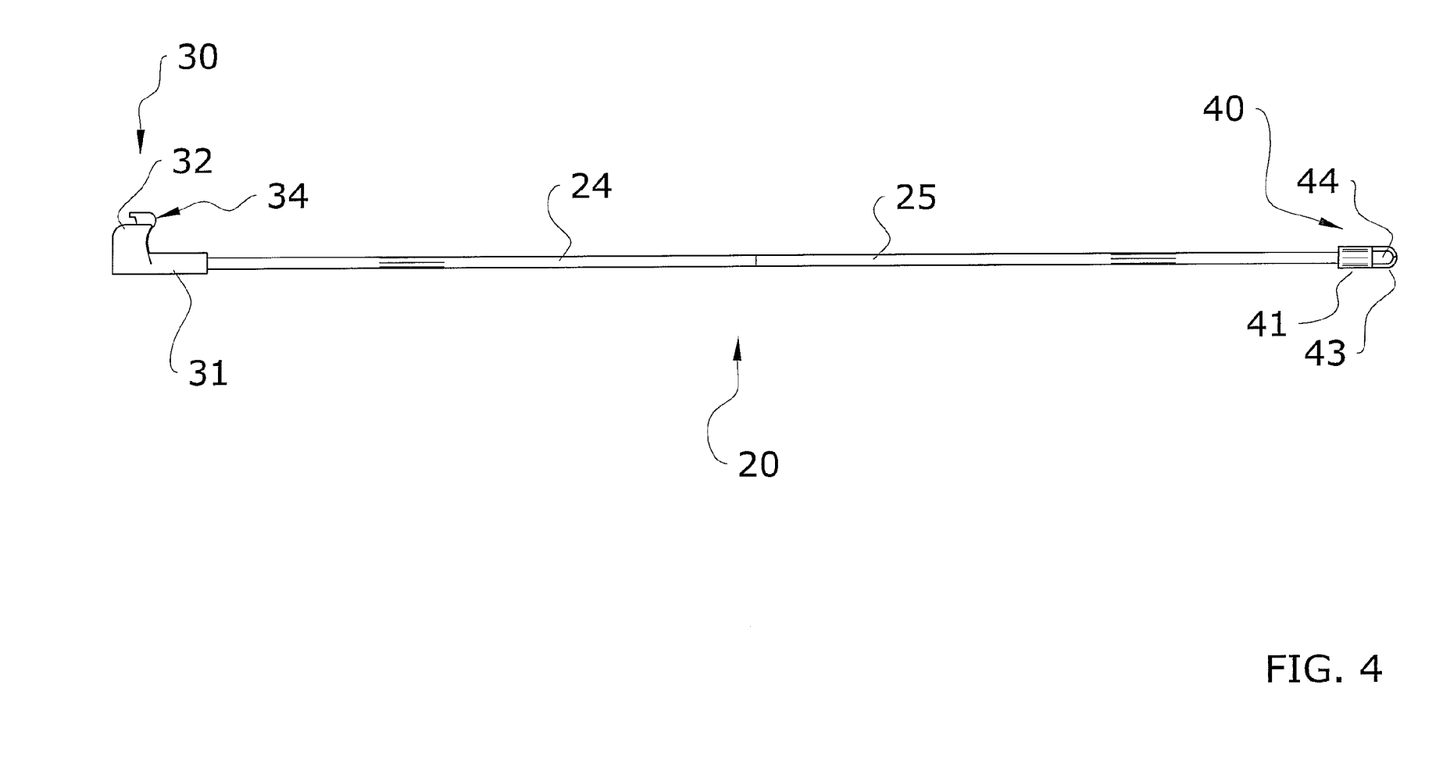
FIG. 4 is a side view of the device.
Figure 5:
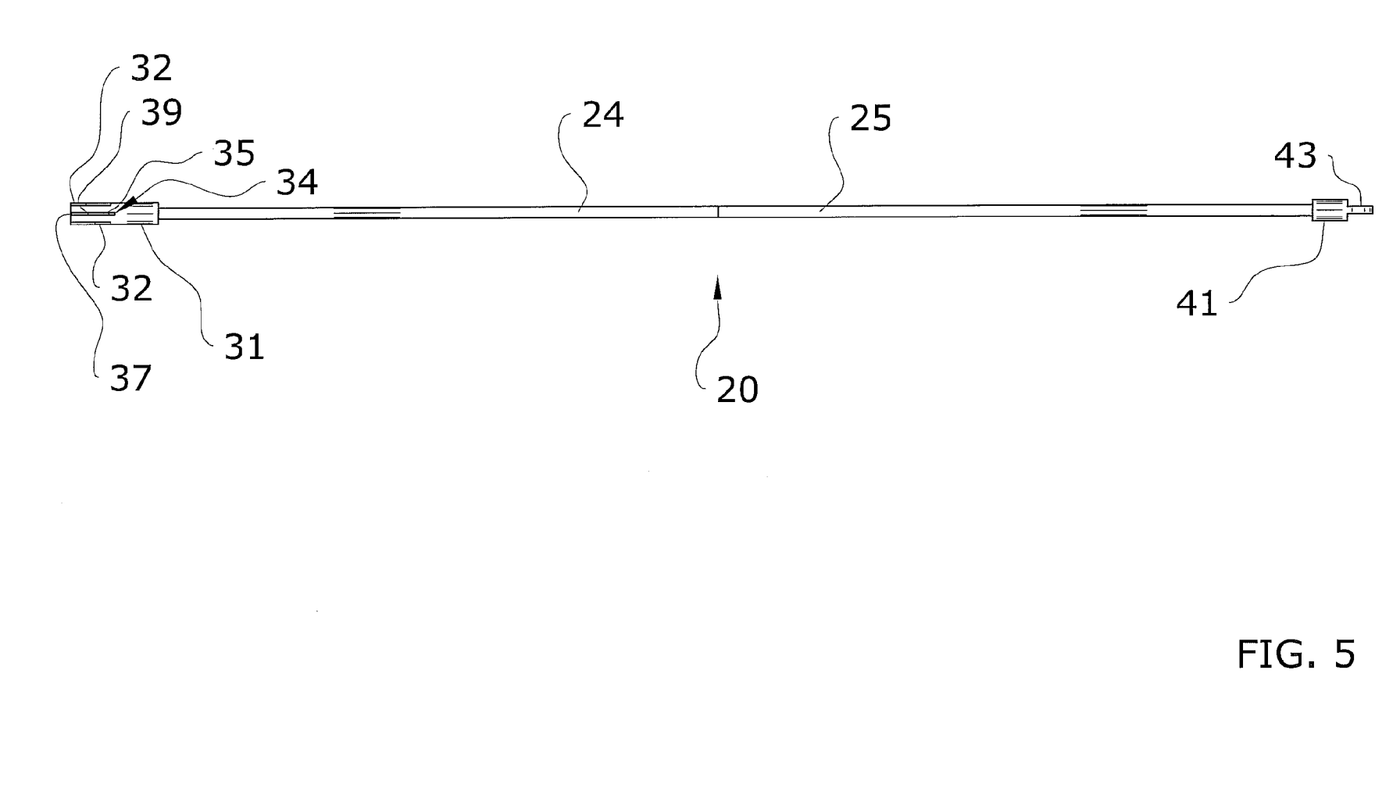
FIG. 5 is a top view of the device.
Figure 6:
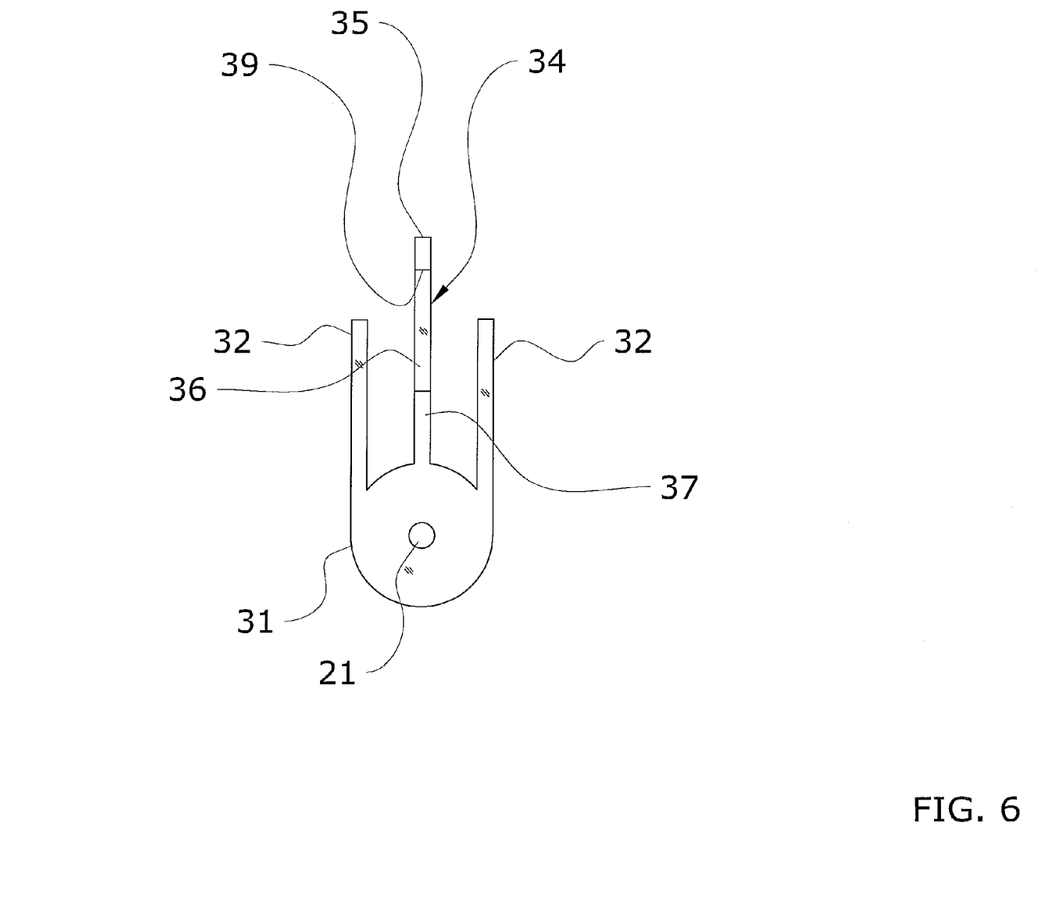
FIG. 6 is a first end view of the device.
Figure 7:
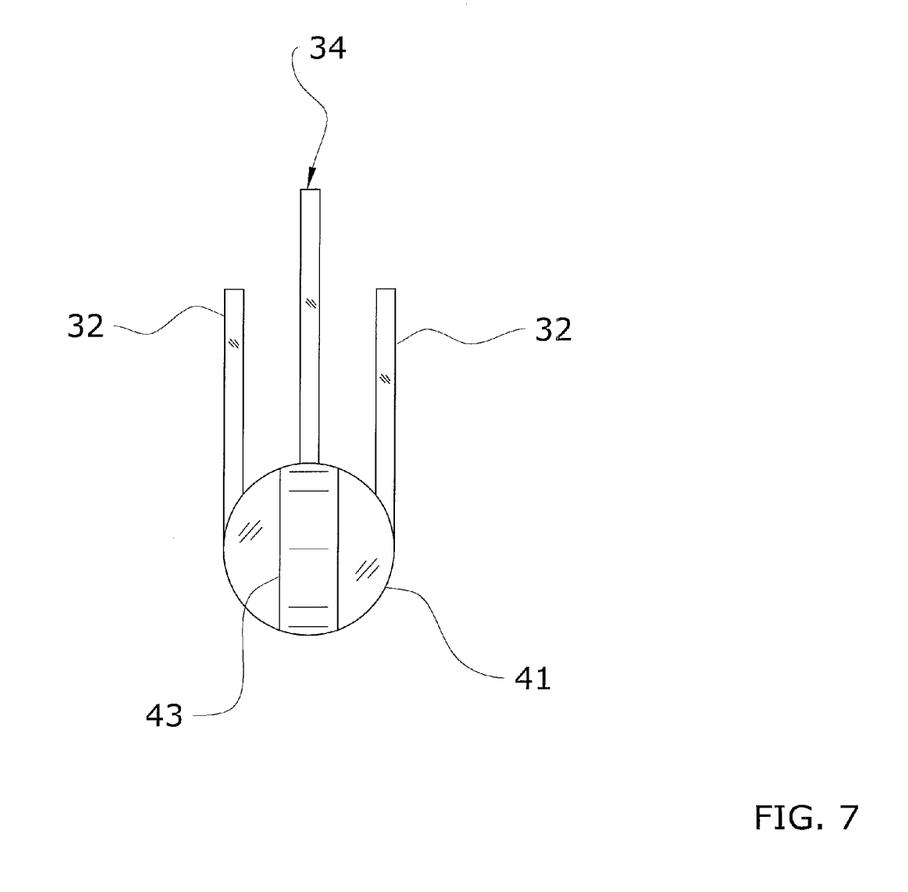
FIG. 7 is a second end view of the device.
Figure 8:
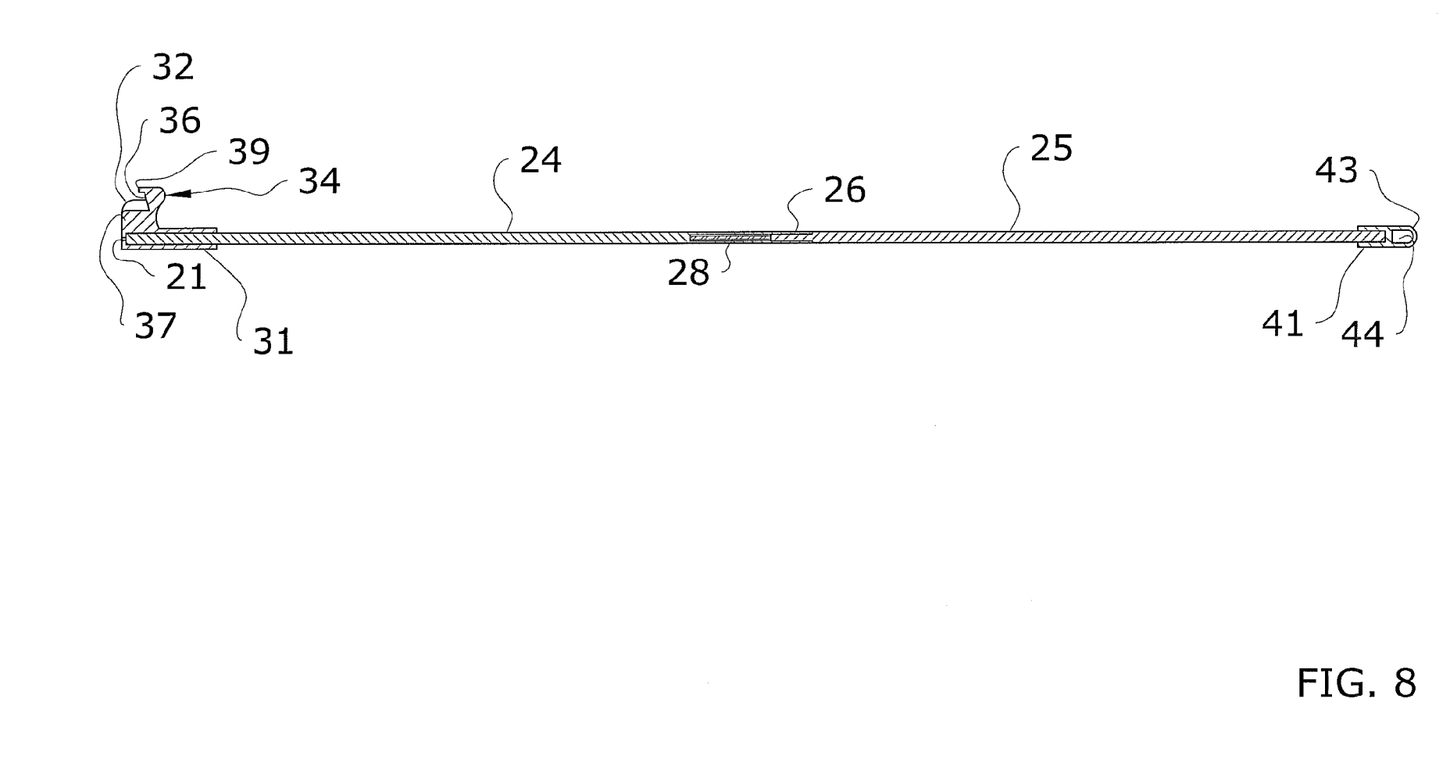
FIG. 8 is a side cross-sectional view of the device.

Generally, the present invention includes the first strap 50 located at the first end 21 to wrap around the center brace 34 via being positioned within the notch 36 and secure the lower end of the leg 12 to the device 10 preferably near the ankle. The present invention also includes the second strap 51 which is extended through the opening 44 of the second support 40 to secure the device 10 to the upper end of the leg 12 preferably near the groin. The present invention further preferably includes a plurality of intermediary straps 52-54 spaced along the length of the shaft 20 for securing the leg 12 adjacent the thigh, knee, and calf as illustrated in FIG. 3. It is appreciated that more or less straps may be utilized.

F. Operation of Preferred Embodiment

In use, the device 10 is attached to the leg 12 by positioning the device 10 next to the leg 12 with the first support 30 forward of the foot and the second support 40 adjacent the groin. The straps 50-54 are attached as previously discussed and the device is then able to provide traction to the leg 12 and assist in the healing process by maintaining the leg 12 in a substantially straight orientation.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. In case of conflict, the present specification, including definitions, will control. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A traction splint device for applying traction to a broken or fractured leg, comprising:
    an elongated shaft having a first end and a second end, wherein said elongated shaft is adapted to be positioned alongside a leg of a patient;
    a first support connected to said first end of said elongated shaft;
    wherein said first support includes a center brace extending therefrom and wherein said center brace has a notch angling downwardly and rearwardly from a top surface of said center brace;
    wherein said center brace of said first support is adapted to be positioned forwardly of a lower end of said leg; and
    a plurality of adjustable stabilizing straps traversing said elongated shaft and adapted to constrain said leg with respect to said elongated shaft;
    wherein said at least one said plurality of adjustable stabilizing straps is adapted to wrap around said notch of said center brace to secure said lower end of said leg;

wherein said center brace includes a projecting portion to project forwardly from said top surface of said center brace beyond said notch.

2. The traction splint device of claim 1, wherein said shaft is comprised of a collapsible structure.

3. The fraction splint device of claim 2, wherein said shaft includes a first segment and a second segment separable from said first segment, wherein said shaft includes an internal connector to connect said first segment to said second segment.

4. The traction splint device of claim 3, wherein said internal connector is comprised of a resilient cord.

5. The traction splint device of claim 1, wherein said plurality of adjustable stabilizing straps have a hook and loop securing structure.

6. The fraction splint device of claim 1, wherein said first support includes a pair of outer walls spaced along each side of said center brace.

7. The fraction splint device of claim 6, wherein said center brace extends upwardly beyond said outer walls.

8. The traction splint device of claim 1, including a second support extending from said second end of said elongated shaft.

9. The fraction splint device of claim 8, wherein said second support has an opening extending therethrough for receiving at least one of said plurality of adjustable stabilizing straps.

10. A traction splint device for applying fraction to a broken or fractured leg, comprising:
   an elongated shaft having a first end and a second end, wherein said elongated shaft is adapted to be positioned alongside a leg of a patient;
   wherein said shaft is comprised of a collapsible structure;
   a first support connected to said first end of said elongated shaft;
   wherein said first support includes a center brace extending therefrom and wherein said center brace has a notch angling downwardly and rearwardly from a top surface of said center brace;
   wherein said center brace of said first support is adapted to be positioned forwardly of a lower end of said leg; and
   a first adjustable stabilizing strap adapted to secure said first end of said elongated shaft adjacent said lower end of said leg, wherein said first adjustable stabilizing strap is positioned around said notch of said center brace and adapted to engage said lower end of said leg;
   a second adjustable stabilizing strap adapted to secure said second end of said elongated shaft adjacent an upper end of said leg, wherein said second adjustable stabilizing strap is positioned around said second end of said elongated shaft and adapted to engage said upper end of said leg; and
   at least one third adjustable stabilizing strap adapted to wrap around an intermediary portion of said elongated shaft between said first end and said second end and engage said leg;
   wherein said shaft includes a first segment and a second segment separable from said first segment, wherein said shaft includes an internal connector to connect said first segment to said second segment.

11. The fraction splint device of claim 10, wherein said adjustable stabilizing straps have a hook and loop securing structure.

12. The fraction splint device of claim 10, wherein said center brace includes a projecting portion to project forwardly from said top surface of said center brace beyond said notch.

13. The fraction splint device of claim 10, wherein said internal connector is comprised of a resilient cord.

14. The fraction splint device of claim 10, wherein said first support includes a pair of outer walls spaced along each side of said center brace.

15. The fraction splint device of claim 14, wherein said center brace extends upwardly beyond said outer walls.

16. The traction splint device of claim 10, including a second support extending from said second end of said elongated shaft.

17. The traction splint device of claim 16, wherein said second support has an opening extending therethrough for receiving said second adjustable stabilizing strap.

18. A traction splint device for applying traction to a broken or fractured leg, comprising:
   an elongated shaft having a first end and a second end, wherein said elongated shaft is adapted to be positioned alongside a leg of a patient;
   a first support connected to said first end of said elongated shaft;
   wherein said first support includes a center brace extending therefrom and wherein said center brace has a notch angling downwardly and rearwardly from a top surface of said center brace;
   wherein said center brace of said first support is adapted to be positioned forwardly of a lower end of said leg;
   a plurality of adjustable stabilizing straps traversing said elongated shaft and adapted to constrain said leg with respect to said elongated shaft;
   wherein said at least one said plurality of adjustable stabilizing straps is adapted to wrap around said notch of said center brace to secure said lower end of said leg; and
   a second support extending from said second end of said elongated shaft, wherein said second support has an opening extending therethrough for receiving at least one of said plurality of adjustable stabilizing straps.

19. The traction splint device of claim 18, wherein said shaft is comprised of a collapsible structure.

20. A fraction splint device for applying traction to a broken or fractured leg, comprising:
   an elongated shaft having a first end and a second end, wherein said elongated shaft is adapted to be positioned alongside a leg of a patient;
   wherein said shaft is comprised of a collapsible structure;
   wherein said shaft includes a first segment and a second segment separable from said first segment, wherein said shaft includes an internal connector to connect said first segment to said second segment;
   wherein said internal connector is comprised of a resilient cord;
   a first support connected to said first end of said elongated shaft;
   wherein said first support includes a center brace extending therefrom and wherein said center brace has a notch angling downwardly and rearwardly from a top surface of said center brace;
   wherein said center brace includes a projecting portion to project forwardly from said top surface of said center brace beyond said notch;
   wherein said first support includes a pair of outer walls spaced along each side of said center brace;
   wherein said center brace extends upwardly beyond said outer walls;
   wherein said center brace of said first support is adapted to be positioned forwardly of a lower end of said leg;

a second support extending from said second end of said elongated shaft, wherein said second support has an opening extending therethrough;

a first adjustable stabilizing strap adapted to secure said first end of said elongated shaft adjacent said lower end of said leg, wherein said first adjustable stabilizing strap is positioned around said notch of said center brace and adapted to engage said lower end of said leg;

a second adjustable stabilizing strap adapted to secure said second end of said elongated shaft adjacent an upper end of said leg, wherein said second adjustable stabilizing strap is positioned through said opening of said second support and adapted to engage said upper end of said leg; and at least one third adjustable stabilizing strap adapted to wrap around an intermediary portion of said elongated shaft between said first end and said second end and engage said leg;

wherein said adjustable stabilizing straps have a hook and loop securing structure.

* * * * *